US006372443B1

(12) United States Patent
Jacobs et al.

(10) Patent No.: US 6,372,443 B1
(45) Date of Patent: Apr. 16, 2002

(54) CASSETTE FOR EXPRESSING A TOXOPLASMA GONDII P30 PROTEIN

(75) Inventors: Eric Jacobs, Dorlisheim; Nathalie Silvestre, Strasbourg; Bruno Mougin; Odette Bissardon, both of Lyons; Michel Jolivet, Bron, all of (FR)

(73) Assignees: Transgene S.A., Strasbourg; Biomerieux, Marcy-l'Etoile, both of (FR)

(*) Notice: Subject to any disclaimer, the term of this patent is extended or adjusted under 35 U.S.C. 154(b) by 0 days.

(21) Appl. No.: 08/604,986

(22) PCT Filed: Jul. 13, 1995

(86) PCT No.: PCT/FR95/00942

§ 371 Date: Mar. 13, 1996

§ 102(e) Date: Mar. 13, 1996

(87) PCT Pub. No.: WO96/02654

PCT Pub. Date: Feb. 1, 1996

(30) Foreign Application Priority Data

Jul. 13, 1994 (FR) .............................. 94 08760

(51) Int. Cl.[7] ...................... G01N 33/53; G01N 33/569; G01N 33/537; C07K 1/00
(52) U.S. Cl. .................. 435/7.22; 435/7.92; 435/7.93; 435/7.94; 435/7.95; 435/962; 530/350
(58) Field of Search .............................. 435/7.22, 7.92, 435/7.93, 7.94, 7.95, 962, 972, 69.1; 536/23.1; 530/350, 387.1, 388.1, 388.6

(56) References Cited

U.S. PATENT DOCUMENTS

| 4,877,726 A | * | 10/1989 | Suzuki et al. |
| 5,407,822 A | * | 4/1995 | Leplatois et al. |
| 5,578,453 A | * | 11/1996 | McDonald et al. |
| 5,629,414 A | * | 5/1997 | Boothroya et al. |
| 5,643,718 A | * | 7/1997 | Kim et al. |

FOREIGN PATENT DOCUMENTS

| EP | A-0353111 | 6/1989 |
| WO | 95/03400 | 2/1995 |

OTHER PUBLICATIONS

Cesborn et al. J. Immunological Methods. 1985. 83, 151–158.*
Velge–Roussel et al (Molecular & Biochemical Parasitology vol. 66 pp 31–38), Jul. 1, 1994.*
Velge–Roussel et al (Annales De Recherches Veterinaries vol. 23(2) pp291–292, 1992.*
Proceedings of the National Academy of Sciences, USA, vol. 91, No. 13, 1994 Washington US, pp. 6186–6190, G. Ketner et al, "Efficient Manipulation of the Human Adenovirus Genome as an Efficious Yeast Artificial Chromosome Clone".
Journal of Biotechnology, vol. 39, No. 2, 1995 Amsterdam NL, E. Degryse, "Evaluation of *Escherichia Coli* recBC sbcBC Mutants for Cloning by Recombination in Vivo".
Virus Research, vol. 28, No. 2, 1993, pp. 153–170, J. Schorr & Doerfler, "Non–homologous Recombination Between Adenovirus and AcNPV DNA Fragments in Cell–free Extracts from Insect Spodoptera Frugiperda Nuclei".
Science, vol. 196, No. 4286, 1977 Lancaster, PA US, M. Perricaudet et al, "Excision and Recombination of Adenovirus DNA Fragments in *Escherichia Coli*".
Nucleic Acids Research, vol. 21, No. 4, 1993, pp. 817–821, A.C. Boyd, "Turbo Cloning: A Fast Efficient Method for Cloning PCR Products and Other Blunt–Ended DNA Fragments Into Plasmids".
Yeast, vol. 11, No. 7, 1995, pp. 629–640, Degryse et al, "In Vivo Cloning by Homologous Recombination in Yeast Using a Two–Plasmid–Based System".
Journal of Molecular Biology, vol. 227, No. 1, 1992, pp. 72–80 Luisi–De Luca, & Kolodner, "Effects of Terminal Non–homology on Intromolecular Recombination of Linear Plasmid Substrates in *Escherichia Coli*".
Proceedings of the National Academy of Sciences of USA, vol. 90, No. 15, Sep. 1993 Washington US, pp. 7356–7360, Tatzelt et al, "Fractionated Nuclear Extracts from Hamster Cells Catalyze Cell–Free Recombination at Selective Sequence Between Adenovirus DNA and a Hamster Preinsertion Site".
Gene Therapy, vol. 2, No. 4, Jun. 1995, pp. 263–268, Imler et al, "An Efficient Procedure to Select and Recover Recombinant Adenovirus Vectors".
Nucleic Acids Research, vol. 21, No. 15, Jul. 25, 1993 Oxford, GB, pp. 3601–3602, P. Bubeck et al, "Rapid Cloning by Homologous Recombination In Vivo".
Methods: A Companion to Methods in Enzymology, vol. 5, 1993, pp. 161–175, F. Spencer et al, "Targeted Recombination–Based Cloning and manipulation of Large DNA Segments in Yeast".
"Conformationally appropriate expression of the toxoplasma antigen SAG1 (p30) in CHO cells", Infection and Immunity, vol. 62, No. 1, Janvier 1994, Washington US, pp. 203–209, Kami Kim et al.

(List continued on next page.)

Primary Examiner—Mark Navarro
(74) Attorney, Agent, or Firm—Burns, Doane, Swecker & Mathis, L.L.P.

(57) ABSTRACT

The present invention provides a reagent for the detection or monitoring of a *Toxoplasma gondii* infection, which includes as a reactive substance a truncated *Toxoplasma gondii* P30 protein in which all of the hydrophobic C-terminal region of the native protein starting with the amino acid positioned after the amino acid 299 (SEQ ID NO: 1) has been deleted and all of the region of the native protein having the sequence starting with amino acid 31 and ending with the amino acid 299 (SEQ ID NO: 1) is contained. The present invention further describes methods of screening for anti-Toxoplasma antibodies in a biological sample.

8 Claims, 3 Drawing Sheets

OTHER PUBLICATIONS

Figure 1:
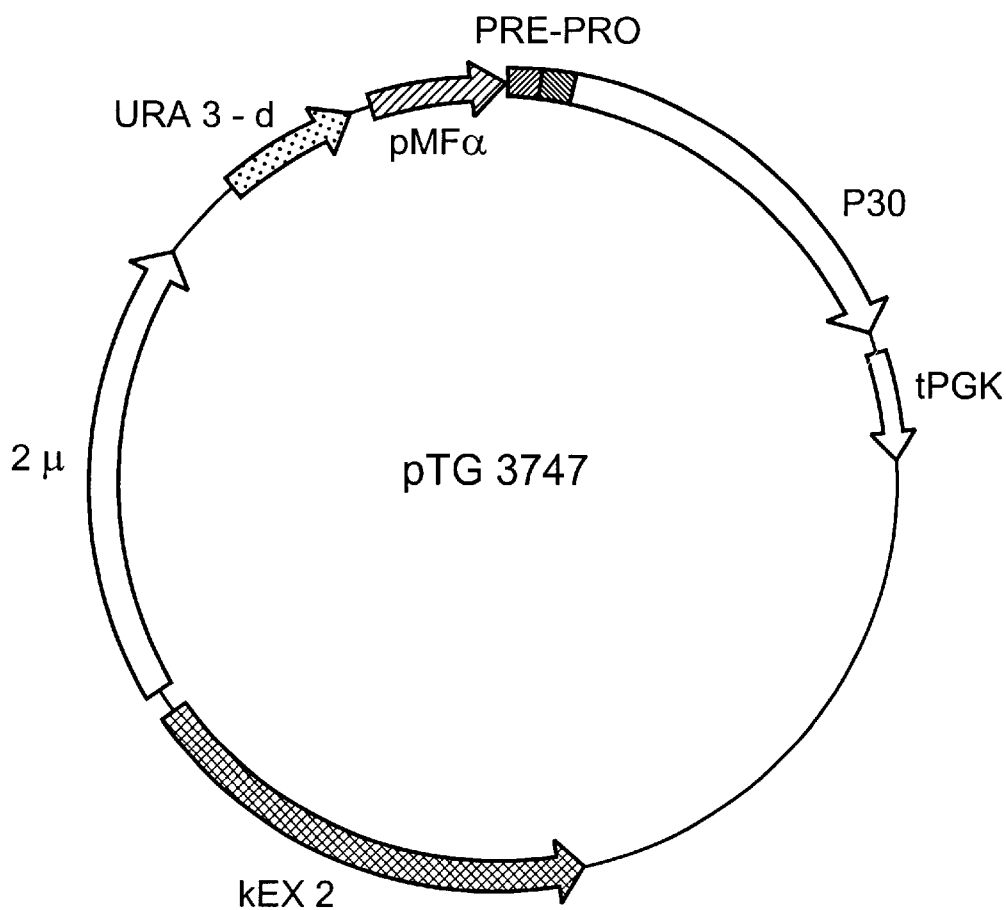
Figure 2:
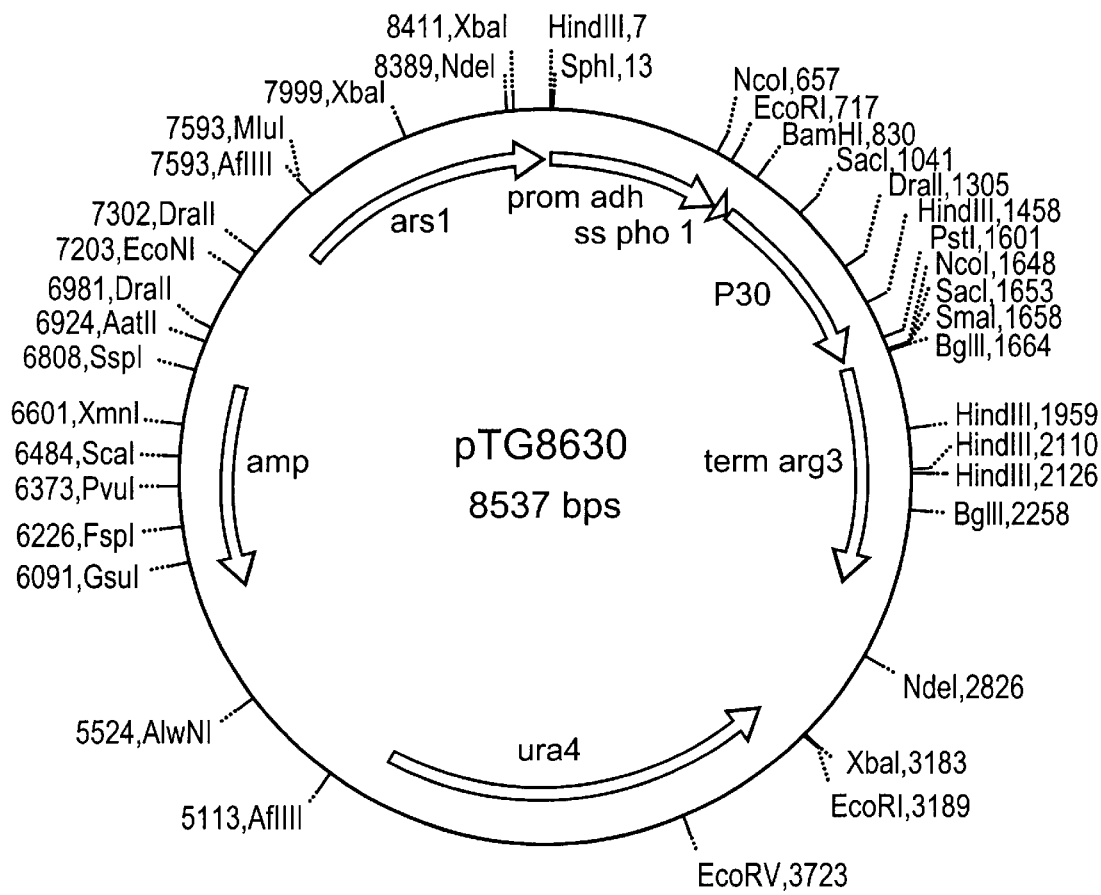
Figure 3:
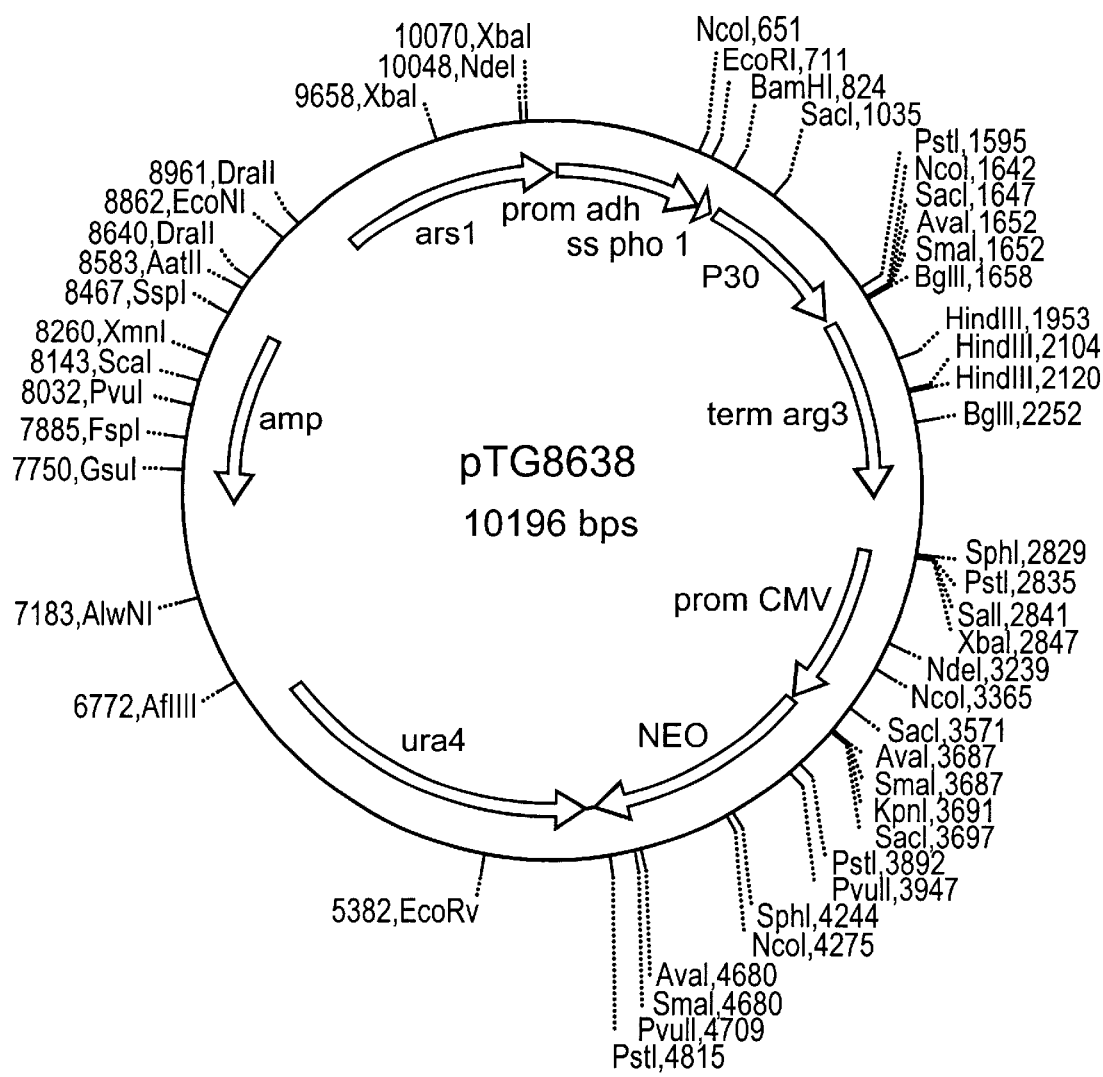

"An unexpected response to vacation with a purified major membrane tachyzoite antigen (P30) of *Toxoplasma gondii*", Journal of Immunology, vol. 134, No. 5, May 1985, Baltimore US, pp. 3426–3431, Lloyd H. Kasper et al.

"Molecular analysis of the gene encoding the major surface of *Toxoplasma gondii*", Journal of Immunology, vol. 141, No. 10, Nov. 15, 1988, Baltimore US, pp. 3584–3591, J. Lawrence Burg et al.

\* cited by examiner

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
    (A) LENGTH: 299 amino acids
    (B) TYPE: amino acid
    (C) STRANDEDNESS:
    (D) TOPOLOGY: linear (ii) MOLECULE TYPE: protein (iii) HYPOTHETICAL: NO (iv) ANTI-SENSE: NO (vi) ORIGINAL SOURCE:
    (A) ORGANISM: Toxoplasma gondii P30 protein
    (B) STRAIN: RH strain (ix) FEATURE:
    (A) NAME/KEY: Cleavage-site
    (B) LOCATION: 30..31
    (D) OTHER INFORMATION: /label= secretion
        /note= "secretory signal between residues 1 to 30 inclusive"

(ix) FEATURE:
    (A) NAME/KEY: Peptide
    (B) LOCATION: 1..30
    (D) OTHER INFORMATION: /label= secretion (xi) SEQUENCE DESCRIPTION: SEQ ID NO:1:

```
Met Phe Pro Lys Ala Val Arg Arg Ala Val Thr Ala Gly Val Phe Ala
1               5                   10                  15

Ala Pro Thr Leu Met Ser Phe Leu Arg Cys Gly Val Met Ala Ser Asp
                20                  25                  30

Pro Pro Leu Val Ala Asn Gln Val Val Thr Cys Pro Asp Lys Lys Ser
                35                  40                  45

Thr Ala Ala Val Ile Leu Thr Pro Thr Glu Asn His Phe Thr Leu Lys
50                  55                  60

Cys Pro Lys Thr Ala Leu Thr Glu Pro Pro Thr Leu Ala Tyr Ser Pro
65                  70                  75                  80

Asn Arg Gln Ile Cys Pro Ala Gly Thr Thr Ser Ser Cys Thr Ser Lys
                85                  90                  95

Ala Val Thr Leu Ser Ser Leu Ile Pro Glu Ala Glu Asp Ser Trp Trp
                100                 105                 110

Thr Gly Asp Ser Ala Ser Leu Asp Thr Ala Gly Ile Lys Leu Thr Val
                115                 120                 125

Pro Ile Glu Lys Phe Pro Val Thr Gln Thr Phe Val Val Gly Cys
                130                 135                 140

Ile Lys Gly Asp Asp Ala Gln Ser Cys Met Val Thr Val Thr Val Gln
145                 150                 155                 160

Ala Arg Ala Ser Ser Val Val Asn Asn Val Ala Arg Cys Ser Tyr Gly
                165                 170                 175

Ala Asp Ser Thr Leu Gly Pro Val Lys Leu Ser Ala Glu Gly Pro Thr
                180                 185                 190

Thr Met Thr Leu Val Cys Gly Lys Asp Gly Val Lys Val Pro Gln Asp
                195                 200                 205

Asn Asn Gln Tyr Cys Ser Gly Thr Thr Leu Thr Gly Cys Asn Glu Lys
                210                 215                 220

Ser Phe Lys Asp Ile Leu Pro Lys Leu Thr Glu Asn Pro Trp Gln Gly
225                 230                 235                 240

Asn Ala Ser Ser Asp Lys Gly Ala Thr Leu Thr Ile Lys Lys Glu Ala
                245                 250                 255
```

```
Phe Pro Ala Glu Ser Lys Ser Val Ile Ile Gly Cys Thr Gly Gly Ser
            260                 265                 270

Pro Glu Lys His His Cys Thr Val Lys Leu Glu Phe Ala Gly Ala Ala
        275                 280                 285

Gly Ser Ala Lys Ser Ala Ala Gly Thr Ala Ser
    290                 295
```

(2) INFORMATION FOR SEQ ID NO:2:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: synthetic oligonucleotide 1367

(xi) SEQUENCE DESCRIPTION: SEQ ID NO:2:

```
GCATGCAAGC TTGGATAAAA AGATCGGATC CCCCTCTTG                    39
```

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: synthetic oligonucleotide 1366

(xi) SEQUENCE DESCRIPTION: SEQ ID NO:3:

```
GCGTCAGTCG ACATTCAACT GGCTGTTCC                               29
```

(2) INFORMATION FOR SEQ ID NO:4:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: synthetic oligonucleotide (OTG2781)

(xi) SEQUENCE DESCRIPTION: SEQ ID NO:4:

```
AATTCCATTG TCTTGACTAT CACAAACTTT TAAGTCTTTT CTTTTTTGGA TCCACACCAT    60

GGAGCTCCCG GGAGATCTA                                                 79
```

(2) INFORMATION FOR SEQ ID NO:5:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: synthetic oligonucleotide (OTG2782)

(xi) SEQUENCE DESCRIPTION: SEQ ID NO:5:

AGCTTAGATC TCCCGGGAGC TCCATGGTGT GGATCCAAAA AAGAAAAGAC TTAAAAGTTT     60

GTGATAGTCA AGACAATGG                                                 79

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: synthetic oligonucleotide 722

(xi) SEQUENCE DESCRIPTION: SEQ ID NO:6:

TCTGGTTAGA TCTAAAAAAT GTCTCCGAAG                                      30

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: synthetic oligonucleotide 723

(xi) SEQUENCE DESCRIPTION: SEQ ID NO:7:

AAAAATGAGA TCTTAACTGG CTGT                                            24

(2) INFORMATION FOR SEQ ID NO:8:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: synthetic oligonucleotide (OTG4096)

(xi) SEQUENCE DESCRIPTION: SEQ ID NO:8:

GATCCAGATC TAAAATGTTC TTGCAAAATT TATTCCTTGG CTTTTTGGCC GTCGTTTGTG    60

CCAACGCGTC G    71

(2) INFORMATION FOR SEQ ID NO:9:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: synthetic oligonucleotide (OTG4097)

(xi) SEQUENCE DESCRIPTION: SEQ ID NO:9:

GATCCGACGC GTTGGCACAA ACGACGGCCA AAAAGCCAAG GAATAAATTT TGCAAGAACA    60

TTTTAGATCT G    71

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: synthetic oligonucleotide (OTG5829)

(xi) SEQUENCE DESCRIPTION: SEQ ID NO:10:

GGCAGGGTCA AGCTTCGAG    19

(2) INFORMATION FOR SEQ ID NO:11:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: synthetic oligonucleotide (OTG2872)

(xi) SEQUENCE DESCRIPTION: SEQ ID NO:11:

GATCCAACCA CATAATGTTC TTGCAAAATT TATTCCTTGG CTTTTTGGCC GTCGTTTGTG    60

CCAACGCGTG AGCT                                                              74

(2) INFORMATION FOR SEQ ID NO:12:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (vi) ORIGINAL SOURCE:
        (A) ORGANISM: synthetic oligonucleotide (OTG2873)

(xi) SEQUENCE DESCRIPTION: SEQ ID NO:12:

CACGCGTTGG CACAAACGAC GGCCAAAAAG CCAAGGAATA AATTTTGCAA GAACATTATG           60

TGGTTG                                                                      66

(2) INFORMATION FOR SEQ ID NO:13:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: synthetic oligonucleotide (OTG3569)

(xi) SEQUENCE DESCRIPTION: SEQ ID NO:13:

TTTGGGCATG CGTCTTTTGA TGCTAAATAA ATTAAATTGT TGG                              43

(2) INFORMATION FOR SEQ ID NO:14:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: synthetic oligonucleotide (OTG3239)

(xi) SEQUENCE DESCRIPTION: SEQ ID NO:14:

GAGAAATACC ACTTAACTTC ATGGATCCCG AGAAAAAACA ATG                              43

(2) INFORMATION FOR SEQ ID NO:15:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
             (A) ORGANISM: synthetic oligonucleotide (OTG3210)

(xi) SEQUENCE DESCRIPTION: SEQ ID NO:15:

CCCAAACCAT GGCAATCAAT CCGGATATCT GCTAAC                                36

(2) INFORMATION FOR SEQ ID NO:16:

(i) SEQUENCE CHARACTERISTICS:
            (A) LENGTH: 58 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: synthetic oligonucleotide (OTG6438)

(xi) SEQUENCE DESCRIPTION: SEQ ID NO:16:

GGGTCAGCAA AATCGGCTGC GGGAACAGCT AGCCACCATC ACCATCACCA CTGAACCC        58

(2) INFORMATION FOR SEQ ID NO:17:

(i) SEQUENCE CHARACTERISTICS:
            (A) LENGTH: 62 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (vi) ORIGINAL SOURCE:
             (A) ORGANISM: synthetic oligonucleotide (OTG6439)

(xi) SEQUENCE DESCRIPTION: SEQ ID NO:17:

GGGTTCAGTG GTGATGGTGA TGGTGGCTAG CTGTTCCCGC AGCCGATTTT GCTGACCCTG       60
CA                                                                     62

(2) INFORMATION FOR SEQ ID NO:18:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: synthetic oligonucleotide (OTG10055)

(xi) SEQUENCE DESCRIPTION: SEQ ID NO:18:

-continued

```
GATCATCATC ACCATCACCA TCATCAC                                        27
```

(2) INFORMATION FOR SEQ ID NO:19:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: synthetic oligonucleotide (OTG10094)

(xi) SEQUENCE DESCRIPTION: SEQ ID NO:19:

```
GATCGTGATG ATGGTGATGG TGATGAT                                        27
```

CASSETTE FOR EXPRESSING A TOXOPLASMA GONDII P30 PROTEIN

The subject of the present invention is a system for expressing a *Toxoplasma gondii* surface antigen, the antigen thus obtained and its use for diagnostic and/or therapeutic purposes.

Toxoplasmosis is an infectious disease caused by a *Toxoplasma gondii* protozoal parasite, a member of the class Sporozoa and of the order Coccidia. *Toxoplasma gondii* is an intracellular parasite which reproduces in a wide variety of cell types inside its hosts, which are mammals.

This parasite, which is very widespread geographically, is an important pathogen, not only in human medicine, but also in veterinary medicine.

In man, two forms of the parasite have been described: the "tachyzoite", which is the multiplicative form encountered during the acute phase of the disease and the "bradyzoite", a resistant form which persist encysted in the nervous tissues, and which is probably responsible for maintaining a durable immunity to reinfection.

In humans, toxoplasmosis is most often asymptomatic and most often passes unnoticed without any consequences. There are however cases in which a Toxoplasma infection or a reactivation of a previously acquired infection can generate serious disorders for the so-called at risk individuals who are pregnant women and immunodepressed or immunosuppressed subjects. This organism has multiple replication sites. However, it may be responsible for severe cerebral and ocular impairments when its replication site is the cells of the central nervous system and the cells of the reticuloendothelial system. Pregnant women represent high-risk subjects, since a Toxoplasma infection, especially during the first few months of pregnancy, may be responsible for serious foetal and neonatal complications if maternal treatment is not undertaken early and pursued assiduously. In particular, newborns contaminated via the transplacental route are subject to serious ocular and cerebral disorders which are even fatal in certain cases. Immunodepressed patients and particularly AIDS patients are subject to serious toxoplasmosis due most often to reactivations of previous infections.

It was therefore essential to have available diagnostic tests which make it possible to determine the presence of the parasite, especially in pregnant women, either by detecting antibodies which may be present in the individual, or by detecting the presence of Toxoplasma antigens in the subject.

HUGUES in "Current topics in Microbiology and Immunology", Vol. 120 (1985), SPRINGER Ed., pages 105–139 has listed a number of commercially available serodiagnostic tests such as the SABIN and FELDMAN staining test, standardized by BEVERLY and BEATTLE in 1958 and perfected by FELDMAN and LAMB (1966), WALDELAND (1976) and BALFOUR et al. (1982); the REMINGTON (1968) test for the detection of antibodies by immunofluorescence, optimized in 1975 by KARIM and LUDLAM; the hemagglutination tests; the ELISA test for the detection of antibodies specific for Toxoplasma, by the isolation of IgM in situ on a microplate described in 1983 by WIELARRD et al.

The different tests used are based on the detection of antibodies or antigens specific for toxoplasmosis. One of the critical points therefore consisted in the characterization of the *Toxoplasma gondii* major antigens which induce a specific immune response and are capable of being used in serological detection tests.

In this regard, Burg et al. (Abstract c85 J. Cell. Biochem., 1986, 1017, 145) have described the exploitation of an expression library in *E. coli* using the complementary DNA (cDNA) obtained from *Toxoplasma gondii* messenger RNAs and the isolation, from this bank, of sequences encoding the antigens present at the surface of the parasite, with the aid of polyclonal antisera directed against the purified surface antigenic proteins P30 and P22

Some authors have shown that P30 constitutes the major surface antigen (see Kasper et al., J. Immunol. 1983, 130, 2407–2412) and can be used for the production of vaccines or in diagnostic tests especially in immunoassays. Moreover, Boothroyd et al. (see Patent Application WO 89/08700) have identified and obtained the genetic material encoding *Toxoplasma gondii* P30 protein and suggest the use of the gene for the production of recombinant protein, peptides and antibodies. This gene has been cloned (Burg et al., 1988, J. Immunol., 141, 3584–3591). Analysis of the sequence shows a secretory signal positioned at the N-terminal end which is cleaved in the mature P30 protein and a highly hydrophobic C-terminal region which is also cleaved and replaced by a glycolipid which allows its membrane anchorage, and a potential N-glycosylation site.

There remains, however, a problem which consists in producing sufficient quantities of the P30 antigen both for the preparation of vaccines and for use in immunological tests. Kim et al. (Infection and Immunity, January 1994, 62, 203–209) have described the expression of a recombinant P30 with a conformation similar to that of the native protein in CHO cells without, however, succeeding in obtaining satisfactory expression levels.

There is, moreover, an advantage in producing a P30 which is secreted into the culture medium in order to facilitate its production and its use for the preparation of diagnostic tests or of pharmaceutical compositions.

Consequently, the subject of the present invention is an expression cassette which is functional in a cell derived from a nonmammalian eukaryotic organism allowing the expression of a DNA fragment encoding a *Toxoplasma gondii* P30 protein, placed under the control of the elements necessary for its expression, said P30 protein being secreted from said cell derived from a eukaryotic organism and recognized by human antisera.

In general, any cell derived from a nonmammalian eukaryotic organism can be used within the framework of the present invention and most particularly an insect cell or a cell derived from a lower eukaryotic organism. The term "cell derived from a lower eukaryotic organism" refers to a cell derived from a unicellular or pluricellular eukaryotic organism not possessing a mechanism which allows cell differentiation. Such cells are known to a person skilled in the art. There will be preferably used, however, a fungus, especially a unicellular fungus, or a yeast, especially of the strain Kluyveromyces, Pichia, Hasegawaea, Saccharomyces or Schizosaccharomyces and most particularly selected from the group consisting of *Saccharomyces cerevisiae, Schizosaccharomyces pombe, Schizosaccharomyces malidevorans, Schizosaccharomyces sloofiae, Schizosaccharomyces octosporus* and *Hasegawaea japonicus*. Of course, these examples are not limiting. A large number of these cells are commercially available in collections such as ATCC (Rockville, Mass., USA) and AFRC (Agriculture and Food Research Council, Norfolk, UK).

For the purposes of the present invention, said cell may be of the wild type or mutant type. In this context, an auxotrophic mutant cell is particularly preferred which has lost the capacity to synthesize at least one metabolite essential for its growth, such that it can grow only in a medium supplemented with this specific metabolite or by complementation with a gene allowing its synthesis. Although a large number of auxotrophy mutations for various essential metabolites are currently known, there may be mentioned more particularly the mutations inhibiting the synthesis of arginine, of leucine and of uracil. Such mutations are described in the literature which is accessible to persons skilled in the art. A large number of auxotrophy mutations affecting various biosynthesis pathways can generally be generated by applying the following approach. Briefly, it is sufficient to cultivate culture the wild-type cells treated with the aid of a mutagen, at the same time in the presence and in the absence of the targeted essential metabolite and to search for the mutants which will multiply only in its presence contrary to the wild-type cells which can grow in both cases.

An expression cassette according to the invention is intended for the production of a P30 protein in a form which is secreted from the cell derived from a non-mammalian eukaryotic organism and which is recognized by anti-Toxoplasma antisera. Such antisera are obtained from patients who have contracted a recent or distant toxoplasmosis containing immunoglobulins which recognize the *Toxoplasma gondii* antigens and especially P30. It goes without saying that said P30 protein can also be recognized by other antibodies directed against the natural P30 protein, such as for example monoclonal or polyclonal antibodies obtained by immunizing a variety of species with the natural protein.

P30 protein is understood to mean the *Toxoplasma gondii* surface antigen produced by the genetic recombination techniques described in the present application or any fragment or mutant of this antigen provided that it is immunologically reactive with antibodies directed against the P30 protein of this parasite. Advantageously, such a protein has an amino acid sequence exhibiting a degree of homology of at least 70%, preferably of at least 85% and, most preferably, of at least 95% compared with the sequence specified by Burg et al. (1988, supra). In practice, such an equivalent may be obtained by deletion, substitution and/or addition of one or more amino acids of the native protein. Persons skilled in the art know the techniques which make it possible to carry out these modifications without affecting immunological recognition.

A DNA fragment in use for the purposes of the present invention may be obtained by any technique in use in the field of the art, for example by cloning a *Toxoplasma gondii* genomic DNA library or a complementary DNA (cDNA) library with an appropriate probe, by PCR (Polymerase Chain Reaction) or alternatively by chemical synthesis.

Within the framework of the present invention, use will be made of a P30 protein in which all or part of the hydrophobic C-terminal region has been amputated and which comprises the elements appropriate to allow secretion, such as for example a secretory signal. Of course, the latter may be homologous, that is to say derived from the native P30 protein. In this context, a preferred expression cassette according to the invention will allow the production of a P30 protein having the sequence as shown in the sequence identifier NO: 1 starting with the amino acid +1 and ending with the amino acid +299. As mentioned above, it may also be a mutant or a fragment of said P30 protein.

Alternatively, a heterologous secretory signal, that is to say one derived from any secreted or membrane protein, can also be used provided, however, that it is functional in the considered cell derived from a non-mammalian eukaryotic organism. According to this variant, an expression cassette according to the invention comprises a DNA fragment encoding a P30 protein having the sequence as shown in the sequence identifier NO: 1 starting with the amino acid +31 and ending with the amino acid +299 or a fragment or mutant of said P30 protein, said DNA fragment comprising, in addition, a sequence encoding a heterologous secretory signal. The latter is generally placed upstream of the first N-terminal residue of the mature P30 protein, namely the residue 31 of SEQ ID NO: 1. The choice of a secretory signal is wide and is accessible to persons skilled in the art. By way of example, there may be mentioned that of the major acid phosphatase (pho1) of *Schizosaccharomyces pombe* (Elliot et al., 1986, J. Biol. Chem. 261, 2936–2941) and the pre-pro sequence of the alpha sex pheromone (Mating Factor alpha or MFα) of *Saccharomyces cerevisiae* (Kurjan and Herskowitz, 1982, Cell, 30, 933–934).

According to an advantageous embodiment, an expression cassette according to the invention allows the production of a nonglycosylated *Toxoplasma gondii* P30 protein. Although any conventional method can be used to inhibit N-glycosylation in the considered cell derived from a non-mammalian eukaryotic organism, such as for example the addition of tunicamycin to the culture medium, it is preferred, however, to mutate the potential N-glycosylation site so that it is no longer recognized by the cellular enzymes participating in the glycosylation. To this end, there is preferably used a DNA fragment encoding a P30 protein comprising at least one mutation, said mutation being characterized by the presence of an amino acid residue different from the natural residue in position 241 and/or 243 of the sequence as shown in the sequence identifier NO: 1, provided that the amino acid residue in position 243 is not a threonine. A mutant of the P30 protein which is particularly preferred within the framework of the present invention comprises a glutamine residue in position 241, in place of the natural asparagine residue.

Of course, an expression cassette according to the invention may allow the production of a P30 protein (having an amino acid sequence as specified above) fused with an exogenous component which can aid its stability, its purification or its production. The choice of such a component is wide and accessible to persons skilled in the art. It may especially be an exogenous protein or peptide. There may be mentioned for example the pho1 protein of *Schizosaccharomyces pombe*, β-galactosidase, a chain of lysine residues (poly Lys) or histidine residues (poly His). The fusion may take place at the N- or C-terminus of the P30 protein in use in the present invention.

An expression cassette according to the invention comprises elements necessary for the expression of said DNA fragment in the considered cell derived from a nonmammalian eukaryotic organism. "Components necessary for the expression" is understood to mean all the elements which allow the transcription of a DNA fragment into messenger RNA (mRNA) and the translation of the latter into protein. Among these, the promoter region is of special importance. It can be constitutive, that is to say it can allow a constant transcription level during the entire cell cycle. By way of nonlimiting examples, the promoter regions derived from the genes PGK (3-phosphoglycerate kinase) and MFα of *Saccharomyces cerevisiae* (Hitzeman et al., 1983, Science, 219, 620–625), adh (alcohol dehydrogenase) of *Schizosaccharomyces pombe* (Russel and Hall, 1983, J. Biol. Chem., 258, 143–149) and the baculovirus p39K early promoters (Guarino et al., 1986, J. Virol., 57, 563) and pl2.5K late promoters (Hill-Perkins et al., 1990, J. Gen. Virol., 71, 971–976).

However, it may be advantageous to use a regulable promoter region which makes it possible to vary the transcription levels according to the culture conditions or the cell growth phase depending on the presence of an inducer (activation of transcription) or of a repressor (repression). In general, the regulable promoter regions are derived from regulable genes for which the regulation mechanisms may be highly varied. As regards *Schizosaccharomyces pombe*, there may be mentioned the thermal shock genes whose expression increases with temperature (Gallo et al., 1991, Mol. Cell. Biol., 11, 281–288) and the gene encoding the enzyme fructose diphosphatase (fdp) whose transcription is repressed in the presence of glucose and induced under conditions of deficiency (Hoffman and Winston, 1989, Gene, 84, 473–479). Also entering into this category are the genes which are regulable by thiamine such as the genes pho4 (Yang and Schweingruber, 1990, Curr. Genet., 18, 269–272), nmt1 (Maundrell, 1990, J. Biol. Chem., 265, 10857–10864) and thi2 (Zurlinden and Schweingruber, 1992, Gene, 117, 141–143) whose expression is regulated at the transcriptional level by thiamine, more precisely repressed in the presence of thiamine and induced or derepressed in its absence.

As regards a regulable promoter region, a promoter region regulable by thiamine is preferably most particularly used. The latter may be isolated, by conventional techniques, from genes corresponding to this type of regulation, such as those mentioned above. Of course, it can be modified by mutation, deletion and/or addition of one or more nucleotide (s) compared with the sequence of the native promoter region, provided, however, that these modifications do not drastically alter its regulatory capacity. A fragment of such a promoter region can also be used, especially a fragment comprising the activation and/or repression sequences responsible for the regulation by thiamine. This fragment is placed upstream of a conventional TATA box and a conventional site of initiation of transcription which are capable of initiating transcription in the considered cell derived from a nonmammalian eukaryotic organism. Although a single fragment of the promoter region is sufficient to ensure the regulation by thiamine, it is also possible to envisage, in order to enhance the levels of expression, using several fragments placed in tandem and in any orientation relative to the TATA box.

One particularly advantageous expression cassette according to the invention is that which combines a promoter region derived from the *Schizosaccharomyces pombe* pho4 gene and a DNA fragment encoding a P30 protein as defined above.

On the other hand, an expression cassette according to the invention may, in addition, contain other elements which contribute to the expression of the DNA fragment, especially a transcription termination sequence such as that of the *Schizosaccharomyces pombe* arg3 gene (Van Huffel et al., 1992, Eur. J. Biochem., 205, 33–43) as well as transcription activation sequences.

According to a particularly advantageous embodiment, an expression cassette according to the invention allows the production, in a form secreted from the nonmammalian cell, of at least 0.1 mg/l of a P30 protein, advantageously of at least 0.2 mg/l and preferably of at least 0.3 mg/l.

The present invention also extends to a vector comprising an expression cassette according to the invention. This may be a viral vector and especially a vector derived from a baculovirus, most particularly intended for expression in an insect cell.

It may also be an autonomously replicating plasmid vector and in particular a multicopy vector present between 5 and 500 copies in the host cell, advantageously between 10 and 400 copies and, preferably, between 20 and 300 copies. There may be mentioned, by way of example, the vectors derived from pGEM3 (Weilguny et al., 1991, Gene, 99, 47–54) and pFL20 (Losson and Lacroute, 1983, Cell, 32, 371–377). Moreover, a vector according to the invention may also comprise elements which ensure its replication, such as the origin 2 of *Saccharomyces cerevisiae* or ars of *Schizosaccharonyces pombe* and, optionally, ori of *Escherichia coli*. In addition, it may also comprise a selectable gene, such as (i) a gene allowing the synthesis of an essential metabolite, especially the URA3 or LEU2 gene of *Saccharomyces cerevisiae* and the ura4 or leu1 gene of *Schizosaccharomyces pombe* or (ii) an antibiotic resistance gene.

The present invention also relates to a cell derived from a nonmammalian eukaryotic organism comprising an expression cassette according to the invention either in a form integrated into the cell genome or inserted into a vector. A cell according to the invention has been defined above. There are preferred most particularly an insect cell, a unicellular fungus or a yeast, especially a yeast selected from the group consisting of *Saccharomyces cerevisiae, Schizosaccharomyces pombe, Schizosaccharomyces malidevorans, Schizosaccharomyces sloofiae, Schizosaccharomyces octosporus* and *Hasegawaea japonicus*.

The present invention also relates to a P30 protein produced by an expression cassette, a vector or a cell derived from a nonmanmalian eukaryotic organism according to the invention. Within the framework of the present invention, the P30 protein may be modified in vitro, especially by the addition or deletion of chemical groups, such as phosphates, sugars or myristic acid so as to enhance its stability or the presentation of one or more epitope(s)

The subject of the present invention is also a process for the preparation of a P30 protein, according to which:

(i) a cell derived from a nonmammalian eukaryotic organism is cultured under appropriate conditions; and (ii) said protein secreted from said cell derived from a nonmammalian eukaryotic organism is recovered.

Within the framework of the invention, the P30 protein is recovered directly in the culture medium according to conventional purification techniques such as for example hydrophobic interaction or ion-exchange chromatography, gel filtration or immunopurification.

As regards the variant according to which the P30 protein is produced using an expression cassette comprising a promoter region regulable by thiamine and, in particular, derived from the *Schizosaccharomyces pombe* pho4 gene, the cells harboring such a cassette are cultured in a medium supplemented with thiamine when the culture is intended solely for their propagation. As soon as a culture is carried out in order to produce a *Toxoplasma gondii* P30 protein, the cells are transferred to a thiamine-free medium. Such a variant is more particularly intended to be carried out with lower eukaryotic cells. Thus, according to a process of the invention:

(i) a cell derived from a lower eukaryotic organism is cultured under appropriate conditions in the absence of thiamine, and (ii) said protein secreted from said cell derived from a lower eukaryotic organism is recovered.

The present invention also relates to a reagent for the detection and/or the monitoring of a *Toxoplasma gondii* infection, which comprises, as reactive substance, a recombinant protein as defined above.

The above reagent is or will be attached directly or indirectly onto an appropriate solid support. The solid support may be, without limitation, in the form of a cone, a tube, a well, beads or the like.

The term "solid support" as used here includes all materials on which a reagent may be immobilized for use in diagnostic tests. Natural or synthetic materials, chemically modified or otherwise, can be used as solid support, especially polysaccharides such as cellulose materials, for example paper, cellulose derivatives such as cellulose acetate and nitrocellulose; polymers such as vinyl chloride, polyethylene, polystyrenes, polyacrylate or copolymers such as propylene and vinyl chloride polymer, vinyl chloride and vinyl acetate polymer; styrene-based copolymers, natural fibers such as cotton and synthetic fibers such as nylon.

Preferably, the solid support is a polystyrene polymer or a butadiene-styrene copolymer. Advantageously, the support is a polystyrene or a styrene-based copolymer comprising between about 10 and 90% by weight of styrene units.

The attachment of the reagent onto the solid support may be performed in a direct or indirect manner.

In the direct manner, two approaches are possible: either by adsorption of the reagent onto the solid support, that is to say by non-covalent bonds (mainly of the hydrogen, Van der Waals or ionic type), or by establishing covalent bonds between the reagent and the support.

In the indirect manner, an "anti-reagent" compound capable of interacting with the reagent can be attached beforehand (by adsorption or covalent bonding) onto the solid support in order to immobilize the whole onto the solid support. By way of example, there may be mentioned an anti-P30 antibody, provided that it is immunologically reactive with a part of the protein which is different from that involved in the reaction for recognition of the antibodies of the sera; a ligand receptor system, for example by grafting onto the P30 protein a molecule such as a vitamin and by immobilizing, on the solid phase, the corresponding receptor (for example the biotin-streptavidin system). Indirect manner is also understood to mean the preliminary grafting or the insertion, by genetic recombination, of a protein or of a polypeptide at one end of the P30 protein and the immobilization of the latter on the solid support by passive adsorption or covalent bonding of the protein or of the polypeptide.

The invention also relates to a process for the detection of anti-Toxoplasma antibodies in a biological sample, such as a blood sample, from an individual or from an animal likely to be or to have been infected by *Toxoplasma gondii*, according to which at least the following steps are performed:

a mixture is prepared comprising:
i) a reagent as defined above which is or which will be immobilized on a solid support,
ii) the sample,
iii) a labeled anti-immunoglobulin;
the mixture is incubated for a predetermined time;
the solid phase is separated from the liquid phase; and
the possible presence of anti-Toxoplasma antibodies is revealed by measuring the level of labeling in the solid phase.

In one embodiment of the invention,
a mixture is prepared comprising:
i) the reagent immobilized on the solid support, and
ii) the sample;
the mixture is incubated for a predetermined time which allows the formation of an immune complex immobilized on the solid support;
an anti-immunoglobulin labeled under appropriate incubating conditions allowing its reaction with the immobilized immune complex is added;
the solid phase is separated from the liquid phase; and
the possible presence of anti-Toxoplasma antibodies is revealed by measuring the level of labeling in the solid phase.

In another embodiment of the invention, the process for the detection of anti-Toxoplasma antibodies in a biological sample, such as a blood sample, from an individual or an animal likely to be or to have been infected by *Toxoplasma gondii* comprises at least the following steps:

a mixture is prepared comprising:
i) an anti-immunoglobulin which is or which will be attached onto a solid support;
ii) the sample;
iii) a labeled reagent which comprises, as reactive substance, the abovementioned P30 protein;
the mixture is incubated for a predetermined time;
the liquid phase is separated from the solid phase; and
the possible presence of anti-Toxoplasma antibodies is revealed by measuring the level of labeling in the solid phase.

Advantageously, a mixture is prepared, comprising the anti-immunoglobulin attached onto the solid support and the sample,
the mixture is incubated for a predetermined time allowing the formation of an immune complex immobilized onto the solid support;
the liquid phase is separated from the solid phase;
the labeled reagent is added which comprises, as reactive substance, the abovementioned P30 protein; and
the possible presence of anti-Toxoplasma antibodies is revealed by measuring the level of labeling in the solid phase.

By way of example, there may be mentioned, as marker, an enzyme such as horseradish peroxidase, alkaline phosphatase, a radioactive isotope such as $^{125}$I, $^{3}$H, $^{57}$Co, a luminescent marker and the like.

The invention also relates to monoclonal or polyclonal antibodies obtained by the immunological reaction of a human or animal organism to an immunogenic agent consisting of the recombinant P30 protein and their use, as reactive substance, in a reagent for the detection and/or monitoring of a *Toxoplasma gondii* infection in a biological sample, such as a tissue sample; the antibodies being previously labeled with any appropriate marker as defined above.

Accordingly, the subject of the invention is a process for the detection of the *Toxoplasma gondii* P30 protein in a biological sample, such as a tissue sample, from an individual or an animal likely to be or to have been infected by *Toxoplasma gondii*, according to which the sample and a reagent as defined above are brought into contact under appropriate conditions which allow a possible immunological reaction, and the possible presence of an immune complex formed with the above mentioned reagent is detected by measuring the level of labeling in the biological sample.

The subject of the invention is also an active immunotherapeutic composition, especially a vaccinal preparation, which comprises, as active ingredient, a recombinant P30 protein, the active ingredient being optionally conjugated with a pharmaceutically acceptable support, and optionally an excipient and/or an appropriate adjuvant.

The present invention also covers a pharmaceutical composition intended for the treatment or for the prevention of a *Toxoplasma gondii* infection in man or animals, comprising a therapeutically effective quantity of an expression cassette, a vector, a cell derived from a nonmammalian eukaryotic organism or a P30 protein according to the invention or prepared according to a process according to the invention.

The examples below will make it possible to demonstrate other characteristics and advantages of the present invention. These examples are illustrated with reference to the following figures.

FIG. 1 is a schematic representation of the vector pTG3747 for the expression of a *Toxoplasma gondii* P30 protein in *Saccharomyces cerevisiae*.

FIG. 2 is a schematic representation of the vector pTG8630 for the expression of a *Toxoplasma gondii* nonglycosylated P30 protein in a *Schizosaccharomyces pombe* strain auxotrophic for uracil.

FIG. 3 is a schematic representation of the vector pTG8638 for the expression of a *Toxoplasma gondii* P30 protein in a wild-type *Schizosaccharomyces pombe* strain.

EXAMPLES

The constructs described below were prepared according to the general genetic engineering and molecular cloning techniques detailed in Maniatis et al. (1989, Laboratory Manual, Cold Spring Harbor Laboratory Press, Cold Spring Harbor, N.Y.). All the cloning steps using bacterial plasmids are carried out by passage through the *Escherichia coli* (*E. coli*) 5K strain. As for the steps involving an M13-type bacteriophage, they are performed in *E. coli* JM101.

The lithium acetate technique (Ito et al., 1983, J. Bacteriol., 153, 163–168) is used to introduce the different vectors into the *Schizosaccharomyces pombe* and *Saccharomyces cerevisiae* strains. However, any other standard technique can also be used. Moreover, as regards the gene encoding the P30 protein, the position of the nucleotides corresponds to that specified in Burg et al. (1988, supra).

Example 1

Production of a P30 Protein in *Saccharomyces cerevisiae*

1. Construction of the Expression Vector pTG3747.

The sequences encoding the *Toxoplasma gondii* P30 protein are isolated from the prior art plasmid comprising the corresponding gene (P30 gene) stretching at least from nucleotides 334 to 1632. This starting plasmid is designated hereinafter pbM 89.

A DNA fragment encoding a mature P30 protein, free of the natural signal peptide and having a stop codon in the C-terminal part just upstream of nucleotide 1258, is generated by PCR (Polymerase Chain Reaction). The vector pbM89 and the primers 1367 carrying in 5' a HindIII site (SEQ ID NO: 2) and 1366 carrying in 5' a SalI site (SEQ ID NO: 3). In parallel, an SphI-HindIII fragment which comprises the promoter of the MFα gene followed by sequences encoding the pre-pro peptide of the same gene is isolated from the vector M13TG3868. The vector M13TG3868 is derived from the vector M13TG3841, which is described in International Application Publication W090/13646, into which an HindIII site has been introduced in 3' of the pro MFα sequence. Such a modification is within the capability of a person skilled in the art. This SphI-HindIII fragment as well as the HindIII and SalI-digested amplification product are cloned between the SphI and SalI sites of the vector pTG4812. The latter is derived from the vector pTG3828, which is described in European Application EPA 396 436, into which the KEX2 gene encoding an endoprotease capable of cleaving the pre and then pro MFα sequences (sequence indicated in this same European document) has been introduced. pTG3747 is obtained which contains, especially, the MFα promoter directing the expression of a fragment comprising the pre-pro MFα sequences followed by the sequences encoding the mature P30. The selectable gene which allows the isolation of the clones consists of the *Saccharomyces cerevisiae* URA3 gene.

Of course, it is within the capability of a person skilled in the art to redone the P30 gene, previously amplified by PCR, starting with the DNA extracted from *Toxoplasma gondii*, into appropriate plasmids for the production of new constructs.

2. Production of the P30 Protein by *Saccharomyces cerevisiae* pTG3747 is introduced into a yeast strain of the *Saccharomyces cerevisiae* species, such as the TGY 73.4 strain of the MFα, pra1, prb1, prc1, csp1, ura3, his3, pep4-3 genotype. The nontransformed strain develops in a rich medium, for example the YPG medium (1% yeast extract, 1% DIFCO bactopeptone, 2% glucose). After transformation with the vector pTG3747, the Ura+prototrophs are selected on a minimum medium, for example the YNBG medium (containing 0.7% yeast nitrogen bases (Yeast Nitrogen Base DIFCO), 0.5% casamino acids and 1% of glucose). The colonies selected are analyzed in the following manner. After 24 h of preculture in minimum medium, the cells are diluted so as to have an $OD_{600nm}$ of about 1 and the culture is continued under the same conditions for about 72 h. Cells and supernatant are separated by centrifugation.

An aliquot of culture supernatant is precipitated either with trichloroacetic acid (0.3M final) in the case of a recognition with an antibody of animal origin or with PEG-4000 (20% final) in the case of a recognition with an antibody of human origin. The precipitation pellet is taken up in a deposition buffer (about 1/200 of the starting volume) not comprising a reducing agent (-mercaptoethanol or DTT). The analysis is performed by Western blotting after an electrophoretic migration on a 12% SDS-PAGE gel, followed by a transfer onto a nitro cellulose membrane (0.45 μm, Schleicher Schüll). The latter is incubated with a positive anti-Toxoplasma rabbit polyclonal serum, a positive human antitoxo antiserum or the monoclonal antibody 1E1E7 which recognizes an epitope of the P30 protein (Fortier et al., 1991, Eur. J. Microbiol. Infect. Dis., 10, 38–40). The reaction is revealed by an anti-rabbit, anti-human or anti-mouse conjugate labeled with alkaline phosphatase (Immunoresearch).

When the culture supernatants of the TGY 73.4 strain are analyzed, a recombinant P30 protein is detected which exists in the form of a heterogeneous material, probably because of the proteolytic cleavages by the KEX2 enzyme or a high heterogeneity in the glycosylation, but which is nevertheless recognized in Western blotting by positive human anti-Toxoplasma antisera.

Example 2

Production of a P30 Protein in *Schizosaccharomyces pombe*

1. Construction of the Expression Vector pTG8610 (constitutive expression in an auxotrophic strain)

The plasmid pEVp11 (Russell and Nurse, 1986, Cell, 45, 145–153) contains the promoter region of the adh gene of *Schizosaccharomyces pombe* in the form of a 700bp SphI-EcoRI fragment, the EcoRI site being situated in the 5' region of the adh gene, 59bp upstream of the initiator ATG. It is digested with the enzymes EcoRI and HindIII and a synthetic fragment resulting from the reassociation of the single-stranded oligonucleotides OTG2781 and OTG2782

(described in SEQ ID NO: 4 and NO: 5 respectively) is introduced with the aim of completing the adh promoter region up to 11bp upstream of the initiator ATG and of creating appropriate restriction sites which facilitate the subsequent cloning steps. pTG1702 is generated.

A 0.92 kb HpaI-ClaI fragment is isolated from pCVH3 (Van Huffel et al., 1992, Eur J. Biochem., 205, 33–43) and then treated with the Klenow fragment of DNA polymerase. This fragment comprises the last codons of the *Schizosaccharomyces pombe* arg3 gene, followed by the sequence for termination of transcription. It is inserted into pTG1702 digested with HindIII and whose ends have been made blunt by treatment with the Klenow fragment of DNA polymerase, in order to give pTG1746.

pTG1746 is digested with XbaI and treated with the Klenow fragment of DNA polymerase before being digested with BamHI. The fragment comprising the sequences for termination of transcription is introduced into the vector pDW230 digested with EcoRI, subjected to a treatment with the Klenow fragment of DNA polymerase and then digested with BamHI. pTG1751 is obtained.

The vector pDW230 is similar to pDW232 which is described in the literature (Weilguny et al., 1991, Gene, 99, 47–54). They are both derived from pGEM3 into which a replication origin which is functional in *Schizosaccharomyces pombe* (ars1 origin) as well as the *Schizosaccharomyces pombe* ura4 gene has been inserted as selectable marker, the only difference being that the introduction of the fragment carrying the ars1 origin at the level of the NaeI site of pGEM3, giving rise to pDW230, caused a deletion of this site up to the base 2862.

The vector pTG1754 was generated by ligation of the SphI-BamHI fragments of pTG1751 (comprising the sequence for termination of transcription arg3) and of pTG1702 (comprising the adh promoter).

In parallel, the sequences encoding P30, provided with its own secretory signal, are obtained in the following manner: the P30 gene is modified by mutagenesis, so as to generate a consensus initiation sequence for yeast at the level of the second initiator ATG (TAAAAA<u>ATG</u>TCT) and a stop codon at the same position as above. The PCR uses the vector pbM89 as template and the oligonucleotides 722 (SEQ ID NO: 6) and 723 (SEQ ID NO: 7) carrying a BglII site at their 5' end. The BglII-treated amplification product is cloned into the vector pTG2886 linearized with the enzyme BglII. This plasmid is described in European Publication EPA 396 436.1. The recombinant clones are analyzed by HindIII-BamHI enzymatic digestion in order to determine the orientation of the insert relative to the promoter. A clone having the appropriate orientation is designated pTG2886-P30. After digestion with BglII, the fragment containing the sequences encoding the P30 protein, equipped with its own secretory signal, is inserted into the vector pTG1754 previously digested with BamHI. pTG 3733 is obtained.

The sequence encoding the natural secretory signal of the P30 protein (residues +1 to +30 of SEQ ID NO: 1) is replaced by the sequence of the *Schizosaccharomyces pombe* pho1 gene encoding the phosphatase secretory signal. For this, the vector pTG2886-P30 is digested with BamHI and a synthetic fragment having the same protruding ends, carrying an internal BglII site in 5' and resulting from the reassociation of the oligonucleotides OTG4096 and OTG4097 (SEQ ID NO: 8 and 9), is introduced.

The BglII fragment carrying the sequence encoding the pho1 secretory signal followed by the mature P30 (residues +31 to +299 of SEQ ID NO: 1) is isolated from the vector obtained in the preceding step. It is inserted into the BamHI site of the vector pTG1754. The transformants having the correct orientation relative to the adh promoter are selected by EcoRI-BamHI digestion. pTG8610 is generated.

2. Construction of the Expression Vector pTG8630 Encoding a Nonglycosylated P30 Protein (constitutive expression in an auxotrophic strain)

The BamHI-SmaI fragment, containing the P30 sequences, is isolated from pTG8610 and introduced between the same sites of M13TG130 (Kieny et al., 1983, Gene, 26, 91–99) in order to mutate the glycosylation site. M13TG8620 is generated. The mutagenesis is carried out with the aid of a commercial kit according to the recommendations of the supplier (for example Amersham) and using the oligonucleotide OTG5829 (SEQ ID NO: 10). The aim of the mutagenesis is to substitute the asparagine residue in position 241 by a glutamine, while creating an HindIII site, thereby facilitating the selection of the mutants. M13TG8622 is obtained.

The expression vector pTG8630 is prepared by inserting, between the SphI-PstI sites of the vector pTG8610, a first SphI-DraII fragment obtained from pTG8610 and a second DraII-PstI fragment purified from M13TG8622.

3. Construction of the Expression Vector pTG8644 (thiamine-regulable expression in an auxotrophic strain)

A synthetic DNA fragment derived from the re association of the oligonucleotides OTG2872 and OTG2873 (SEQ ID NO: 11 and NO: 12) was inserted between the BamHI and SacI sites of the vector pTG1702 (Example 2.1). pTG1716 is generated which comprises the sequence encoding the *Schizosaccharomyces pombe* major acid phosphatase (pho1) secretory signal downstream of the adh promoter region.

pTG1716 is modified by inserting, between the MluI and HindIII sites, a DNA sequence encoding the Lys47 variant of hirudin (HV2 Lys47). pTG1722 is obtained.

The SphI-SacI fragment comprising the adh promoter region, followed by the sequence encoding the pho1 secretory signal and HV2 Lys47 is isolated from pTG1722. It is then subcloned between the same sites of pTG1751. pTG1757 is obtained therefrom.

Moreover, the promoter region of the *Schizosaccharomyces pombe* pho4 gene is obtained by PCR from the clone pSp4B (Yang and Schweingruber, 1990, Current Genet., 18, 269–272) and with the aid of the primers OTG3569, comprising an SphI site (SEQ ID NO: 13) and OTG3239 equipped with a BamHI site (SEQ ID NO: 14). The SphI-BamHI fragment thus generated is substituted for the SphI-BamHI fragment carrying the adh promoter region of pTG1757 in order to give pTG2734.

A 642 bp fragment containing the 5' flanking seqences of the *Schizosaccharomyces pombe* pho4 gene, which are situated upstream of the TATA box, is isolated by PCR from the vector pTG2734. The primers OTG3569 (SEQ ID NO: 13) and OTG3210 (SEQ ID NO: 15) are used. The SphI-NcoI PCR fragment thus obtained is introduced into pTG1757 digested with the same enzymes in order to give pTG2735.

Finally, the EcoRI fragment isolated from pTG8610 and containing the sequence encoding the P30 protein followed by the arg3 terminator is introduced into the vector pTG2735 digested with EcoRI. The vector pTG8644 is obtained in which the sequences encoding the secretory signal pho1 and the P30 protein (residues +31 to +299 of SEQ ID NO: 1) are under the control of a hybrid promoter consisting of the sequences of the pho4 gene which are responsible for the regulation by thiamine, placed upstream of the TATA box of the adh gene.

4. Construction of the Expression Vector pTG8638 (constitutive expression in a wild-type strain).

The aim is to generate expression vectors such as those of Examples 2.1, 2.2 or 2.3 containing, in addition, a gene allowing selection in a wild-type strain not exhibiting auxotrophy, for example a gene for resistance to an antibiotic, such as the neo (Neomycin) gene which confers resistance to G418.

The neo gene is derived from the vector Tn5 (merck et al., 1982, Gene, 19, 327–336). The latter is modified by conventional mutagenesis techniques in order to create restriction sites which facilitate subsequent cloning steps, such as a BamHI site at the 5' (in position 138) and 3' (in position 1280) ends of the neo gene. The BamHI fragment is treated with the Klenow DNA polymerase before being introduced into the EcoRI site of pDW230 whose ends have been made blunt by treating with Klenow. pTG1796 is obtained.

The neo gene is placed under the control of the CMV (cytomegalovirus) IE1 promoter extending from nucleotides −727 to +78 (Boshart et al., 1985, Cell, 41, 521–530). A BamHI site is introduced in 5' of the promoter and a HindIII site in 3'. The BamHI-HindIII fragment, treated with Klenow DNA polymerase, is inserted upstream of the neo gene into the BamHI site made blunt by treating pTG1796 with Klenow. pTG3777 is generated into which it will be possible to introduce the cassettes for the expression of the P30 protein which are described above.

The SphI-NdeI fragment containing the expression cassette "adh promoter-P30-term arg3" is isolated from pTG8610 and then treated with T4 DNA polymerase. It is cloned into the HindIII site, treated with T4 DNA polymerase, of pTG3777in order to give the vector pTG8638.

5. Production of the P30 Protein in An Auxotrophic *Schizosaccharomyces pombe* Strain.

The expression vectors of Examples 2.1, 2.2 and 2.3 are introduced into a mutant *Schizosaccharomyces pombe* strain, for example the D18 strain which is auxotrophic for uracil and which is available at the AFRC under the reference 2036. The same strain transformed in parallel with the vector pTG1754 is used as negative control. Of course, any other strain having this type of auxotrophy may be suitable.

The strains for which the expression of P30 is constitutive, namely those transformed by the vectors pTG8610 and pTG8630, are cultured at 30° C. in a Kappeli synthetic medium optimized for yeast (Fiechter et al., 1981, Adv., Microbiol. Physiol. 22, 123–183) and supplemented with 2% glucose and a mixture of vitamins.

The strains transformed by the vector pTG8644 are precultured in the same supplemented Kappeli medium. However, the mixture of vitamins comprises especially thiamine at a final concentration of 0.002 g/l (thi$^+$ medium). When the cultures reach an OD (optical density) at 600 nm of between 1 and 2, they are diluted to an OD of about 0.05, either in thi$^+$ medium or in a Kappeli medium supplemented with 2% glucose and a mixture of vitamins free of thiamine (thi$^-$medium). The culture is continued at 30° C. up to the end of the exponential phase.

Aliquots of each of the cultures are collected regularly during the exponential phase as well as at the end of the growth phase. The culture supernatants are analyzed by Western blotting, as described in Example 1.2.

The yeasts transformed by pTG8610 or pTG3733 synthesize and secrete a recombinant P30 which is recognized by any of the three antibodies mentioned above (rabbit antiserum, human antiserum, which are toxopositive, and 1E1E7 antibody). The recombinant P30 is provided in the form of a homogeneous material with a slightly diffused appearance, with an apparent molecular mass (AMM) of about 35 kDa. A more intense signal is observed in the culture supernatant of pTG8610, which indicates that the efficiency of the pho1 secretory signal is greater for the secretion of the P30 protein in *Schizosaccharomyces pombe* than that of the natural P30 signal. It can be noted that, under reducing conditions (the loading buffer contains a reducing agent), the antibodies no longer recognize the recombinant P30, indicating that only conformational epitopes are involved in the recognition in Western blotting, as is observed with the native P30.

Likewise, a production of recombinant P30 protein is detected in the culture supernatants of *Schizosaccharomyces pombe* transformed by pTG8644, this occurring when the culture is carried out in the absence of thiamine. It is revealed by the human antisera and has an AMM of 35 kDa. On the other hand, no product is visualized by these same P30 protein-specific antibodies when the culture is carried out in the presence of thiamine.

The analysis of the supernatants of yeasts transformed by pTG8630, carried out using a toxo-positive rabbit antiserum, reveals a predominant band of about 28 kDa under nonreducing conditions, that is to say about 5 kDa smaller than that observed for the product of expression of pTG8610 or pTG8644. This difference in molecular mass is explained by the fact that the protein is a nonglycosylable protein since it is mutated at the level of the N-glycosylation site.

6. Production of the P30 Protein in a Wild-type *Schizosaccharomyces pombe* Strain.

Various wild-type strains of *Schizosaccharomyces pombe* are available at the AFRC. There may be mentioned, by way of example, the strains 20 286 and 26 760 in which the vector pTG8638 is transformed. The transformants are selected because of their resistance to G418 (concentration of 0.2 to 1 mg/ml). After culture in a selective liquid medium (YPG medium containing neomycin), the culture supernatants are analyzed by Western blotting with the aid of human antisera. A predominant band is detected at the position expected for the glycosylated recombinant P30.

7. Construction of pTG9643 (thiamine-regulable production of a nonglycosylated P30 protein).

The EcoRI fragment isolated from pTG8630 (Example 2.2) and containing the sequence encoding the nonglycosylated P30 followed by the arg3 terminator was introduced into the vector pTG2735 (Example 2.3) digested with EcoRI. pTG9643 is generated. The fusion protein can be produced based on the same technology as that used in Example 2.5.

8. Construction of pTG8667 (thiamine-regulable production of a glycosylated P30 protein fused with a poly His tail at the C-terminus).

The vector pTG8644 (Example 2.3) is digested with PstI and SmaI and a synthetic fragment is introduced which is derived from the reassociation of oligonucleotides OTG6438 and 6439 (SEQ ID NO: 16 and 17). pTG8667 is generated which comprises the pho4/adh hybrid promoter, the sequences encoding the pho1 secretory signal and the P30 protein followed by 6 histidine residues forming a poly His tail. The fusion protein can be produced based on the same technology as that used in Example 2.5.

9. Construction of pTG9618 (thiamine-regulable production of a nonglycosylated P30 protein fused with a poly His tail at the C-terminus).

The BamH1-Pst1 fragment of pTG8667 (containing the glycosylated P30 sequence) is replaced by an equivalent fragment isolated from pTG8630 (nonglycosylated P30). pTG9618 is thus generated. The fusion protein can be produced based on the same technology as that used in Example 2.5.

10. Construction of pTG8221 (thiamine-regulable production of a nonglycosylated P30 protein fused with a poly His tail at the N-terminus).

The plasmid pTG9643 is digested with BamH1 and a synthetic DNA fragment obtained from the reassociation of the oligonucleotides OTG10055 and 10094 (SEQ ID NO: 18 and 19) is cloned at the level of this site. pTG8221 is obtained in which there are 8 histidine residues preceding the P30 protein.

Example 3

Production of a P30 Protein in a Baculovirus

The DNA fragment encoding the P30 protein equipped with its signal peptide is isolated from pTG2886-P30 after digestion with BglII and inserted into a baculovirus vector; for example the vector pACMP1, digested with BamHI (Hill-Perkins and Possee, 1990, J. Gen. Virol., 71, 971–976) or the vector described by Guaniro et al. (1986, J. Virol., 57, 563), in order to give pTG3729 and pTG3731 respectively.

The recombinants are generated as described by J. M. VLAK et al. in Proceedings of the Baculovirus and Recombinant Protein Production Workshop, "Baculovirus and recombinant protein production processes", March 29-April 1, Interlaken, Switzerland.

The supernatants are centrifuged for 10 minutes at 1,000 rpm (revolutions per minute) and stored at −20° C. before being analyzed on 12% SDS-PAGE, followed by Western blotting and by radioimmunoprecipitation.

For the latter technique, the cell culture is labeled with 300 µCi of tran $^{35}$S-label (trade name: ICN Biomedical France ref. 51006) at 1 hour 30 min or 26 hours after the infection. The supernatant is harvested 48 hours after the infection. The immunoprecipitation is performed according to the following procedure. The culture supernatants are centrifuged at 2,000 rpm for 20 min, diluted one half in 2×NET buffer (0.1% NP40, 1 mM EDTA, 50 mM Tris-HCl pH 8.0, 150 mM NaCl, 0.25% gelatin, 0.02% $NaN_3$, 2% aprotinin, 2 mM PMSF) and then immunoprecipitated with either toxo-positive human sera or with 1E1E7 monoclonal antibody for 2 hours at 4° C., and the final addition of protein A Sepharose (Pharmacia). The precipitate is washed successively with the buffers 1×NET, Tris-NP40, 1×PBS (8mM $Na_2HPO_4.12H_2O$, 2 mM $KH_2PO_4$, 150 mM NaCl) and 0.1×PBS. The analysis is carried out after electrophoretic migration on a 12% SDS-PAGE gel and autoradiography. The recombinant P30 is observed in the culture supernatant of the cells infected with the recombinant baculoviruses.

When the culture supernatants are analyzed by Western blotting under nonreducing conditions, both the toxo-positive human sera and the rabbit antiserum recognize a doublet composed of a predominant band with an AMM of about 28 kDa and a minor band with an AMM of about 29 kDa. No significant difference is observed between the recombinant P30 proteins produced by the recombinant viruses. On the other hand, no product is detected under conditions reduced by DTT.

Example 4

Purification of the P30 Protein Produced in *Schizosaccharomyces pombe*

1) Purification by ion-exchange Chromatography (column technique).

The culture supernatants (volume 10 liters) obtained as described in Example 2 are reduced 20 to 50 times by concentrating on hollow fibers or on tangential ultrafiltration cassettes (final volume: 500 to 200 ml) (molecular weight cut-off 10,000 daltons), and dialyzed by this same operation in a 50 mM Tris buffer, pH 8.5 approximately without NaCl or an equivalent buffer, which will be used in the next step.

The second step consists of a conventional ion-exchange chromatography, for example on a column of 100 ml of the gel DEAE TRISACRYL (DEAE: diethylaminoethyl) or Hyper D, (marketed by the company Biosepra) or DEAETSK (Merck) which makes it possible to recover, by a gradient with an ionic strength of 0 to 1M NaCl, the eluates which are tested on an SDS-PAGE gel and analyzed by Western blotting. The analysis makes it possible to reveal the recombinant P30 band of about 30 kD.

In order to perfect the isolation of this recombinant protein, an affinity chromatography step can be performed on a chromatographic support covalently coupled to the anti-P30 1E1E7 monoclonal antibody. After specific elution by varying the pH (pH 2.5 or pH 11.5), the P30 protein peak obtained is of sufficient purity for this protein to be used in diagnostic kits.

When the P30 protein is fused with a polyhistidine tail, at both the N- and C-termini, a metal chelate chromatography step may be included. The supports which are suitable for this technology are known to persons skilled in the art and are commercially available. There may be mentioned, as examples, chelatine Sepharose (Pharmacia) to be charged with metal ions and nickel chelate (NINTA Agarose, Quiagen).

Example 5

Reactivity Towards Antibodies.

The reactivity of the recombinant P30 was tested against 151 known sera of which 95 were given as positive sera and 56 as negative sera, using the VIDAS apparatus (trademark) marketed by the company bioMérieux SA.

1) Reference Test: VIDAS TOXO IgG

The test automated on the Vidas system allows the quantitative measurement of anti-Toxoplasma IgGs in a human serum. The principle of the assay combines the immunoenzymatic method with a final fluorescence detection (ELFA).

All the steps of the reactions are controlled by the instrument. Onto a disposable cone made of K resin (butadiene-styrene copolymer), which serves both as solid phase and as pipetting system, is adsorbed a preparation comprising the *Toxoplasma gondii* membrane and cytoplasmic antigens, this preparation being obtained by sonicating whole Toxoplasma cells. The other reagents necessary for the diagnostic test are pre-distributed into a cartridge combined with the cone. The human serum incubation phase allows the attachment of the anti-Toxoplasma IgGs if they are present; then anti-human IgG globulin (Boehringer ref: 1272 896) labeled with alkaline phosphatase (Boehringer ref: 556 602) is added in order to reveal the presence of these anti-Toxoplasma IgGs which may be present.

The result or titre is expressed in IU/ml (International Units) relative to a calibration curve stored in the Vidas. The results are presented in the table below (see Vidas-Titers column).

2) Microplate Test for the Recombinant P30 Protein

The P30 (5 ng/well) to be tested is attached in the wells of a microtiter plate (Polylabo, ref: 13159). The same human sera which were tested on the VIDAS apparatus as described above were incubated for 1 hour at 37° C., after which a peroxidase-labeled anti-human IgG globulin (ref. 815462) was added in order to reveal the possible serum IgGs reacting against this P30.

The results are given as optical density read at 492 nm and are presented in the table below (see REC P30 column).

| | VIDAS TITERS | REC. P30 OD | | VIDAS TITER | REC. P30 OD | | VIDAS TITERS | REC. P30 OD |
|---|---|---|---|---|---|---|---|---|
| AG 1 | >300 | * | AG 51 | 67 | 1140 | AG 21 | 0 | 180 |
| AG 54 | >300 | 1638 | AG 87 | 58 | 1432 | AG 28 | 0 | 116 |
| AG 73 | >300 | * | AG 44 | 49 | 1309 | AG 38 | 0 | 90 |
| AG 37 | 289 | * | AG 31 | 46 | 1088 | AG 39 | 0 | 207 |
| AG 70 | 268 | 1385 | AG 29 | 41 | 966 | AG 40 | 0 | 105 |
| AG 59 | 243 | 2049 | AG 20 | 35 | 1096 | AG 46 | 0 | 340 |
| AG 10 | 240 | * | AG 22 | 34 | 706 | AG 47 | 0 | 317 |
| AG 64 | 222 | * | AG 25 | 22 | 598 | AG 56 | 0 | 391 |
| AG 72 | 208 | * | AG 4 | 21 | 1129 | AG 58 | 0 | 210 |
| AG 34 | 191 | 1271 | AG 42 | 21 | 609 | AG 60 | 0 | 494 |
| AG 35 | 191 | 1986 | AG 45 | 20 | 708 | AG 61 | 0 | 304 |
| AG 23 | 189 | 1409 | AG 43 | 15 | 677 | AG 65 | 0 | 312 |
| AG 32 | 182 | 1760 | AG 50 | 14 | 1209 | AG 66 | 0 | 214 |
| AG 27 | 172 | * | AG 85 | 14 | 526 | AG 67 | 0 | 251 |
| AG 33 | 156 | * | AG 41 | 10 | 319 | AG 68 | 0 | 170 |
| AG 36 | 153 | 1090 | AG 75 | 10 | 440 | AG 74 | 0 | 119 |
| AG 2 | 153 | 1578 | AG 86 | 9 | 270 | AG 76 | 0 | 335 |
| AG 24 | 153 | 1435 | AG 57 | 7 | 234 | AG 78 | 0 | 433 |
| AG 48 | 128 | 1718 | AG 12 | 3 | 166 | AG 79 | 0 | 250 |
| AG 15 | 114 | 1770 | AG 5 | 0 | 284 | AG 81 | 0 | 189 |
| AG 16 | 107 | * | AG 6 | 0 | 204 | AG 82 | 0 | 202 |
| AG 71 | 105 | 986 | AG 11 | 0 | 376 | AG 83 | 0 | 73 |
| AG 9 | 104 | 1458 | AG 14 | 0 | 160 | AG 89 | 0 | 481 |
| AG 77 | 70 | 1927 | AG 17 | 0 | 550 | | | |
| AG 90 | 61 | 769 | AG 18 | 0 | 98 | | | |
| AG 30 | 60 | 754 | AG 19 | 0 | 433 | | | |
| G 10 | >300 | * | G 99 | >300 | * | G 8 | >300 | * |
| G 13 | >300 | * | G 160 | >300 | * | G 155 | >300 | 2281 |
| G 152 | >300 | * | G 161 | >300 | * | G 165 | >300 | * |
| G 153 | 257 | 2435 | G 162 | >300 | * | G 164 | >300 | * |
| G 169 | 246 | * | G 163 | >300 | * | G 182 | 94 | * |
| G 154 | 228 | 2456 | G 168 | >300 | * | G 189 | 210 | 2365 |
| G 170 | 222 | * | G 159 | 283 | * | G 200 | 168 | * |
| G 180 | 119 | 1981 | G 197 | 187 | * | G 174 | 74 | 1542 |
| G 195 | 99 | 2076 | G 183 | 163 | 2280 | G 119 | 72 | 1407 |
| G 48 | 82 | 1477 | G 178 | 145 | * | G 96 | 71 | 1336 |
| G 158 | 82 | 1544 | G 187 | 142 | 2169 | G 127 | 26 | 944 |
| G 115 | 27 | 1127 | G 202 | 68 | 1702 | G 121 | 24 | 722 |
| G 81 | 17 | 692 | G 157 | 69 | 1568 | G 87 | 21 | 796 |
| G 177 | 13 | 427 | G 198 | 53 | 1532 | G 88 | 20 | 765 |
| G 172 | 12 | 871 | G 104 | 39 | 2464 | G 81 | 16 | 649 |
| G 185 | 12 | 801 | G 100 | 35 | 1212 | G 176 | 16 | 455 |
| G 143 | 5 | 476 | G 126 | 28 | 1269 | G 142 | 5 | 182 |
| G 148 | 2 | 139 | G 115 | 27 | 942 | G 139 | 2 | 417 |
| G 150 | 2 | 318 | G 111 | 24 | 896 | G 133 | 1 | 281 |
| G 151 | 2 | 324 | G 110 | 12 | 319 | G 118 | 0 | 278 |
| G 136 | 1 | 141 | G 173 | 10 | 517 | G 97 | 0 | 304 |
| G 146 | 1 | 155 | G 132 | 4 | 264 | G 204 | 0 | 279 |
| G 93 | 0 | 175 | G 145 | 2 | 409 | o | | |
| G 112 | 0 | 173 | G 141 | 2 | 281 | | | |
| G 138 | 0 | 121 | G 144 | 1 | 390 | | | |
| G 147 | 0 | 131 | G 131 | 1 | 172 | | | |
| | | | G 134 | 0 | 82 | | | |
| | | | G 105 | 0 | 125 | | | |

*means an optical density greater than 2400 (OD expressed as a thousandth) = limit of the reader As can be seen on reading the preceding table, there is a very good correlation between the results obtained with the tests carried out on the VIDAS apparatus in the presence of Toxoplasma membrane and cytoplasmic antigens and those obtained in a conventional microplate assay in the presence of the recombinant P30 protein of the invention.

What is claimed is:

1. A reagent for the detection or monitoring of a *Toxoplasma gondii* infection, which comprises, as reactive substance, a truncated *Toxoplasma gondii* P30 protein secreted by a non-mammalian eukaryotic cell transformed with an expression cassette comprising a DNA fragment encoding said truncated protein, in which:

at least all of the hydrophobic C-terminal region of the native protein starting with the amino acid positioned after the amino acid +299 of the sequence SEQ ID No:1 has been deleted; and at least all the region of the native protein having the sequence starting with the amino acid +31 and ending with the amino acid +299 of the sequence SEQ ID No: 1 is contained, wherein said DNA fragment encoding the truncated *Toxoplasma gondii* P30 protein is placed under the control of elements necessary for said truncated *Toxoplasma gondii* P30 protein expression.

2. A process for the detection of anti-Toxoplasma antibodies in a biological sample from an individual or from an animal likely to have been infected by *Toxoplasma gondii*, which comprises at least the following steps:

preparing a mixture comprising:
  i) the reagent as claimed in claim 1 which is or which will be immobilized on a solid support;
  ii) the sample,
  iii) a labeled anti-immunoglobulin;

incubating the mixture for a predetermined time;

separating the solid phase from the liquid phase; and measuring the level of labeling in the solid phase to detect the presence of anti-Toxoplasma antibodies.

3. The process as claimed in claim 2, wherein:

said mixture comprises:
  i) the reagent immobilized on the solid support; and
  ii) the sample;

incubating the mixture for a predetermined time which allows the formation of an immune complex immobilized on the solid support;

adding a labeled anti-immunoglobulin to said immobilized complex under appropriate incubating conditions and allowing its reaction with said immobilized immune complex;

separating the solid phase from the liquid phase; and measuring the level of labeling in the solid phase to detect the presence of anti-Toxoplasma antibodies.

4. A process for the detection of anti-Toxoplasma antibodies in a biological sample from an individual or from an animal likely to have been infected by *Toxoplasma gondii*, which comprises the following steps:

preparing a mixture comprising:
  i) a first reagent comprising a truncated *Toxoplasma gondii* P30 protein secreted by a non-mammalian eukaryotic cell transformed with an expression cassette comprising a DNA fragment encoding said truncated protein, in which:

at least all of the hydrophobic C-terminal region of the native protein starting with the amino acid positioned after the amino acid +299 of the sequence SEQ ID No:1 has been deleted; and at least all the region of the native protein having the sequence starting with the amino acid +31 and ending with the amino acid +299 of the sequence SEQ ID No: 1 is contained, wherein said DNA fragment encoding the truncated *Toxoplasma gondii* P30 protein is placed under the control of elements necessary for said truncated *Toxoplasma gondii* P30 protein expression wherein said truncated protein is immobilized on a solid support, ii) the sample,
  iii) a second labeled reagent comprising a labeled polyclonal antibody;

incubating the mixture for a predetermined time;

separating the solid phase from the liquid phase; and measuring the level of labeling in the solid phase to detect the presence of anti-Toxoplasma antibodies.

5. A reagent according to claim 1, wherein said DNA fragment comprises in addition a sequence encoding a heterologous secretory signal.

6. A process according to claim 4, wherein in step i) said DNA fragment comprises in addition a sequence encoding a heterologous secretory signal.

7. A process for detection of anti-Toxoplasma antibodies in a biological sample from an individual or an animal likely to be or to have been infected by *Toxoplasma gondii*, which comprises at least the following steps:

preparing a mixture comprising:
   i) an anti-immunoglobulin which is or which will be attached onto a solid support;
   ii) the sample;
   iii) the reagent as claimed in claims 1 or 5, which is labeled;
incubating the mixture for a predetermined time;
separating the liquid phase from the solid phase; and
measuring the level of labeling in the solid phase to detect the presence of anti-Toxoplasma antibodies.

8. The process as claimed in claim 7, wherein:
said mixture comprises:
   i) an anti-immunoglobulin attached onto the solid support;
   ii) the sample;
   iii) the reagent as claimed in claims 1 or 5, which is labeled;
incubating the mixture for a predetermined time allowing the formation of an immune complex immobilized on the solid support;
separating the liquid phase from the solid phase;
adding the reagent as claimed in claims 1 or 5, which is labeled; and
measuring the level of labeling in the solid phase to detect the presence of anti-Toxoplasma antibodies.

* * * * *